United States Patent
Masuda et al.

(10) Patent No.: US 8,211,362 B2
(45) Date of Patent: Jul. 3, 2012

(54) PACKAGED BLOOD PURIFICATION DEVICE

(75) Inventors: Toshiaki Masuda, Osaka (JP); Yuki Hatakeyama, Osaka (JP); Takashi Sunohara, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 10/947,323

(22) Filed: Sep. 23, 2004

(65) Prior Publication Data
US 2005/0063859 A1 Mar. 24, 2005

(30) Foreign Application Priority Data

Sep. 24, 2003 (JP) .................................. 2003-330973
Sep. 24, 2003 (JP) .................................. 2003-330974

(51) Int. Cl.
*A61M 1/00* (2006.01)
*A61M 37/00* (2006.01)
(52) U.S. Cl. .......... 422/44; 422/45; 604/6.09; 604/6.14
(58) Field of Classification Search ........ 604/4.01–6.16; 422/44–48; 210/232
See application file for complete search history.

(56) References Cited

U.S. PATENT DOCUMENTS

| | | | | |
|---|---|---|---|---|
| 4,219,426 A | * | 8/1980 | Spekle et al. | 210/232 |
| 4,374,802 A | * | 2/1983 | Fukasawa | 422/48 |
| 4,708,796 A | * | 11/1987 | Yoshimoto et al. | 210/321.8 |
| 4,813,210 A | * | 3/1989 | Masuda et al. | 53/425 |
| 4,940,541 A | * | 7/1990 | Aoyagi | 210/321.8 |
| 5,160,615 A | * | 11/1992 | Takagi et al. | 210/321.8 |
| 5,294,401 A | * | 3/1994 | Hagiwara | 422/48 |
| 5,881,534 A | * | 3/1999 | Ahlqvist et al. | 53/403 |
| 6,776,912 B2 | * | 8/2004 | Baurmeister | 210/646 |
| 6,846,794 B1 | * | 1/2005 | Ingram et al. | 510/446 |
| 7,087,168 B2 | * | 8/2006 | Oishi et al. | 210/500.23 |

FOREIGN PATENT DOCUMENTS

| | | | |
|---|---|---|---|
| EP | 1344542 A1 | * | 9/2003 |
| JP | 5-50946 B2 | | 7/1993 |
| JP | 6-285162 A | | 10/1994 |
| JP | 2000-288085 A | | 10/2000 |
| JP | 2001-170167 A | | 6/2001 |
| WO | WO-98/58842 A1 | | 12/1998 |

* cited by examiner

*Primary Examiner* — Tatyana Zalukaeva
*Assistant Examiner* — Philip R Wiest
(74) *Attorney, Agent, or Firm* — Birch, Stewart, Kolasch & Birch, LLP

(57) ABSTRACT

A packaged blood purification device including a hollow fiber blood-processing device having a bundle of hollow fibers and a cylindrical container holding the bundle of hollow fibers; and a gas-impermeable container for packaging the hollow fiber blood-processing device. The hollow fiber blood-processing device is sealed together with an oxygen absorber in the gas-impermeable container, and is sterilized with radiation. The blood-processing device is produced by a method including the steps of sealing a hollow fiber blood-processing device in said gas-impermeable container together with an oxygen absorber, and radiation sterilizing the blood-processing device held in the sealed gas-impermeable container.

13 Claims, 1 Drawing Sheet

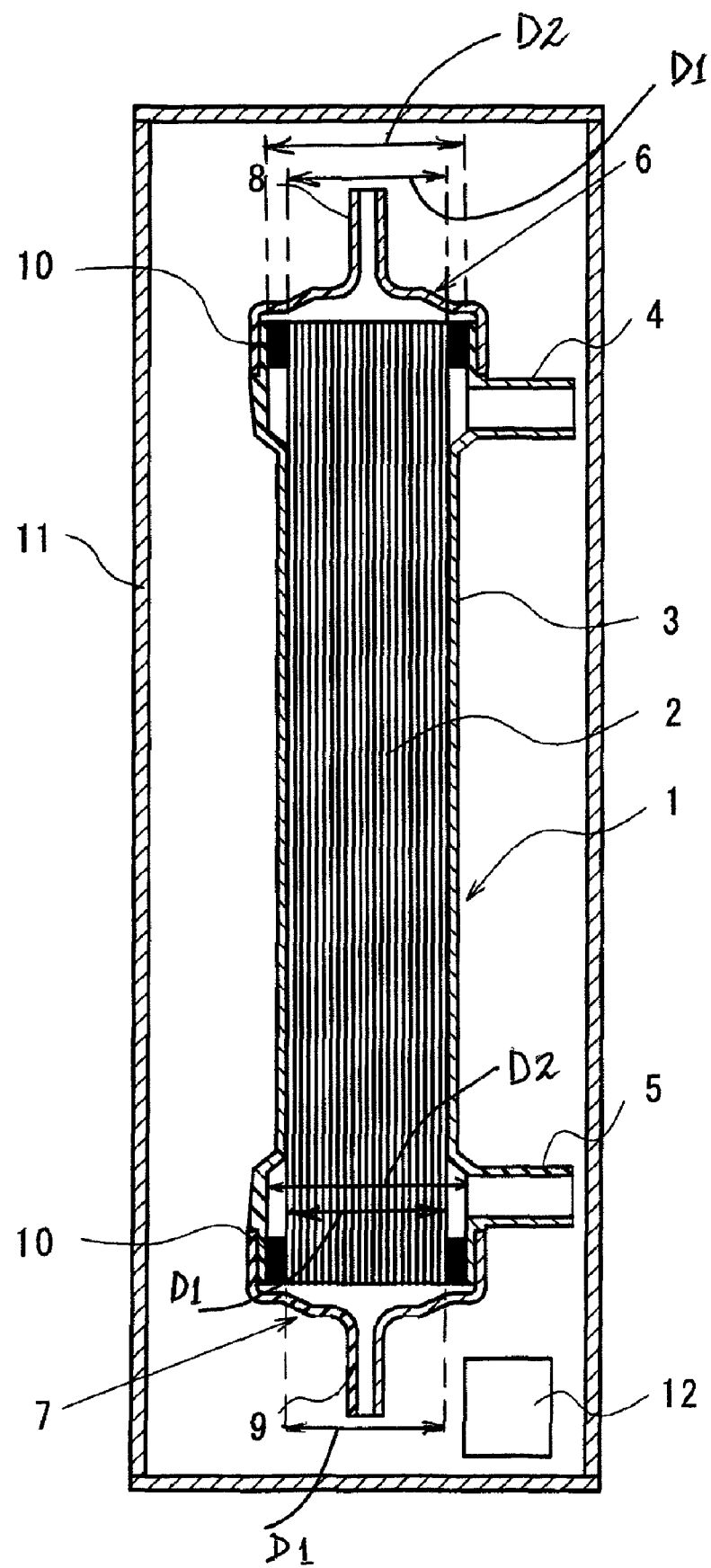

PACKAGED BLOOD PURIFICATION DEVICE

This Nonprovisional applications claims priority under 35 U.S.C. §119(a) on patent application Ser. No(s). 2003-330973 & 2003-330974 filed in Japan on Sep. 24, 2003, the entire contents of which are hereby incorporated by reference.

BACKGROUND OF THE INVENTION

1. Field of the Invention

The present invention relates to a hollow fiber blood-processing device used for blood processing such as hemodialysis, hemofiltration, hemodiafiltration, plasma fraction and plasmapheresis, and a method for packaging and sterilizing such devices.

2. Description of Related Art

It is known that hollow fibers used as filters or semipermeable membranes in the blood-processing devices are generally damaged by radiation sterilization, resulting in increase of eluting materials or extractables from the hollow fibers. In particular, the hollow fibers of polysulfone-based resins including hydrophilic polymer have a high tendency to be damaged by irradiation. The extractables from the hollow fibers are measured by absorbance of a test solution for extraction, of which measuring procedures and criterion measure are defined in approval standards for artificial kidneys. In the standard, a test solution for extraction is prepared by placing 1.5 g of dry hollow fibers cut to a length of 2 cm and 150 mL of distilled water for injection in a glass container that meets alkali elution test defined in "Test procedures for glass containers for injections" in "The Japanese Pharmacopoeia Fourteenth Edition; warming the solution at 70±5° C. for 1 hour, cooling the solution to the room temperature, removing the hollow fibers from the solution, and then adding distilled water to the solution to adjust its volume to 150 ml. The absorbance is determined at the maximum absorption length within the range of 220 to 350 nm by ultraviolet absorption spectrum of the solution. The criterion measure for absorbance is set to 0.1 or below.

Up to now, there have been proposed a few methods for preventing hollow fibers of the hollow fiber blood-processing devices from being damaged by radiation sterilization. For example, Japanese patent laying-open No. JP2000-288085A (Patent document 1) discloses a method for preventing hollow fibers from being damaged by irradiation, which comprises the steps of controlling a water content of hollow fibers to ≦5%, and a relative humidity of ambient atmosphere to ≦40% when carrying out radiation sterilization. Japanese patent laying-open No. JP2001-170167A (Patent document 2) discloses a method that comprises the steps of allowing hollow fibers to hold water accounting for 100 to 600% of the whole weight of the hollow fibers, and filling the blood-processing device with inert gas. Japanese patent publication No. H5-50946 (B) discloses a method comprising the steps of sealing a blood-processing device together with deoxidizer in a gas-impermeable container, and then subjecting the resultant sealed container to radiation sterilization.
Patent document 1: JP2000-288085A
Patent document 2: JP2001-170167A
Patent document 3: JP H05-050946B

SUMMARY OF THE INVENTION

However, when the radiation sterilization is applied to the hollow fiber blood-processing devices, the methods of the prior art have troubles in arrangements of radiation sterilization since they require strict control of the water content of the hollow fibers and relative humidity of the ambient atmosphere thereof, or processes of allowing hollow fibers to hold water and filling the interior of the blood-processing device with inert gas.

On the other hand, it has now been found that if the hollow fiber blood-processing device is sealed together with the deoxidizer in the gas-impermeable container as disclosed in the above Patent document 3, the hollow fibers are damaged by irradiation, resulting in increase of extractables from the hollow fibers. In particular, if the hollow fibers are of polysulfone-based resin containing hydrophilic polymer, the extractables are considerably increased, resulting in failure to meet the above criterion measures.

It is therefore an object of the present invention to provide a hollow fiber blood-processing device, which has been reduced in extractables from the hollow fibers after radiation sterilization.

Another object of the present invention is to provide a method for packaging and sterilizing hollow fiber blood-processing devices, which enables to minimize damages of hollow fibers caused by radiation sterilization.

The present invention has been made on the finding that oxygen deteriorates quality of hollow fibers, especially those of polysulfone-based resin and promotes damages of hollow fibers during radiation sterilization.

According to the present invention, there is provided a hollow fiber blood-processing device comprising a bundle of hollow fibers and being sealed in a gas-impermeable container together with a deoxidizer and radiation sterilized, characterized in that said deoxidizer is a water-releasing type deoxidizer.

A material for the hollow fibers used in the blood processing device may be a polysulfone-based resin containing a hydrophilic polymer. Preferred polysulfone-based resin includes polysulfone and polyethersulfone. A preferred hydrophilic polymer is polyvinylpyrrolidone.

According to the present invention, there is also provided a method for packaging and sterilizing hollow fiber blood-processing devices of the kind wherein said device comprises a bundle of hollow fibers and is sealed in a gas-impermeable container, said method comprising the steps of sealing a hollow fiber blood-processing device together with a deoxidizer of a water-releasing type in a gas-impermeable container, and radiation sterilizing said blood-processing device held in the sealed gas-impermeable container.

In a preferred embodiment, the hollow fiber blood-processing device comprises a bundle of hollow fibers made of a polysulfone-based resin containing a hydrophilic polymer.

When applying radiation sterilization to the gas-impermeable container holding the hollow fiber blood-processing device and the deoxidizer, it is preferred that the interior of the blood-processing device and that of the container are in the oxygen free condition. To this end, the sealed container holding the blood-processing device is left to stand for a time sufficient to allow the deoxidizer to absorb oxygen in the container after sealing of the container.

The blood-processing device of a hollow fiber type may be of a dry type.

The radiation sterilization may be gamma-radiation sterilization.

In the present invention, the term "blood-processing device" generally means a medical apparatus used for blood processing such as hemodialysis, hemofiltration, hemodiafiltration, plasma fraction and plasmapheresis.

The term "hollow fiber blood-processing device" means an apparatus of the kind wherein a plurality of yarns referred to as "hollow fibers" of various synthetic resins are bundled to form a hollow fiber bundle and wherein the hollow fiber bundle is housed in a cylindrical container. The hollow fibers are required to have a property to selectively allow blood components to filter out, and to have an excellent biocompatibility including antithrombogenicity. The materials for hollow fibers that comply with these requirements include natural cellulose, derivatives thereof such as cellulose diacetate, cellulose triacetate; high polymers prepared by copolymerization of a hydrophilic monomer and a hydrophobic monomer; and blends of hydrophilic polymer and polysulfone-based resin. It is to be noted, however, that the present invention is never limited by the material for hollow fibers and may be applied to any blood-processing device comprising hollow fibers of any desired material.

In one embodiment of the present invention, the hollow fiber blood-processing device comprises hollow fibers made of polysulfone-based resin containing hydrophilic polymer. The polysulfone-based resin includes, for example, polysulfone and polyethersulfone.

In the present invention, the hydrophilic polymer is a polymer that is present in hollow fibers of polysulfone-based resin and provides the hollow fibers with hydrophilicity. Such hydrophilic polymer includes, for example, polyvinylpyrrolidone (hereinafter referred to as "PVP") and polyethylene glycol. Among them, preferred hydrophilic polymer is PVP in view of the efficacy of hydrophilicity and safety to use. The hydrophilic polymer used in the present invention has a molecular weight of 10,000 to 1,200,000, preferably, 50,000 to 500,000. Further, it is preferred that a content of the hydrophilic polymers in the hollow fibers is 3 to 20% by weight, preferably, 3 to 10% by weight in respect to the total weight of the hollow fibers. Examples of commercially available PVP are PVPK-15, 30, 60, 90(Trade name of ISP).

The hollow fibers may be manufactured by incorporating hydrophilic polymer into a concentrate solution for spinning, and then spinning yarns by dry or wet spinning. For example, the hollow fibers are manufactured by the steps of mixing polysulfone, hydrophilic polymer, a solvent thereof, an additive for controlling a pore size of micropores of the hollow fibers with stirring at an elevated temperature to prepare a homogeneous concentrate solution for spinning; extruding the resultant spinning solution comprises of polysulfone and hydrophilic polymer into a gas atmosphere through a ring portion of a double ring nozzle while expelling a lipophilic liquid such as liquid paraffin as a core liquid through a central portion of the nozzle, or feeding a gas such as nitrogen to form a hollow fiber as well as to form miropores in the hollow fibers.

The solvent used is a solvent that is able to dissolve both polysulfone-based resin and hydrophilic resin. Examples of usable solvents are N-methyl-2-pyrrolidone, dimethylsulfoxide and N-dimethylacetamide. These solvents may be used alone or in combination to adjust the solubility. A preferred content of the solvent in the spinning solution ranges from 35 to 75 percent by weight.

The above solvent may be blended with a liquid as a nonsolvent that does not possess the solubility for both polysulfone-based resin and hydrophilic resin to adjust the solubility. Such a nonsolvent include, for example, polyvalent alcohols such as monoethylene glycol, triethylene glycol, polyethylene glycol and glycerin; and lower alkylether derivatives of these polyvalent alcohols; which may be used alone or in combination with two or more materials. The nonsolvent is preferably added to the spinning solution in the range of 7 to 35 percent by weight.

The additive for controlling pore size of the micropores includes, for example, liquid paraffin, isopropyl myristate, air, helium gas and nitrogen gas.

The gas atmosphere into which the spinning solution is extruded includes, without being limited to, air, nitrogen, oxygen, carbon dioxide, argon and helium. Generally, the atmosphere is air.

Preferably, the hollow fibers used in the blood-processing device have an internal diameter ranging from 100 to 300 μm. If the internal diameter is less than 100 μm, it induces increase in pressure loss of the blood flowing through the hollow fibers, which gives rise to damages of the blood, causing a risk of destruction of red blood cells. Further, the internal diameter less than 100 μm may cause coagulation of the blood, causing a possibility of formation of a blood clot in the hollow portions. On the other hand, if the internal diameter exceeds 300 μm, hollow portions of the hollow fibers become too large to keep their hollow shape, resulting in decrease of productivity. In addition, the internal diameter exceeding 300 μm considerably reduces a shearing rate at an inner surface of the hollow fiber membrane, and thus proteins in the blood have the tendency to accumulate on the inner surface. Preferably, the hollow fibers have an inner diameter ranging from 120 to 250 μm.

It is preferred that the hollow fibers have a film thickness ranging from 10 to 50 μm. More preferred film thickness of the hollow fibers ranges from 10 to 30 μm.

The above hollow fibers may be modularized in a known manner, for example, by a method comprising the steps of bundling about 7000 to 12000 pieces of hollow fibers to form a hollow fiber bundle; inserting the resultant hollow fiber bundle into a cylindrical container; injecting a potting material into both ends of the container to seal each end of the container; cutting off the excess potting material together with the hollow fibers from each end of the container to open both ends of the hollow fibers, and mounting headers on each end of the container to complete a hollow fiber module.

As to materials for other components of the blood-processing device other than the hollow fibers, e.g., the cylindrical container and potting material, it is preferred to use such materials that they are little deteriorated by irradiation. Typical materials for the cylindrical container are exemplified by polycarbonate and polypropylene, but it is preferred to use polycarbonate that is excellent in both thermostability and transparency. Typical materials for the potting material are exemplified by polyurethane, epoxy resin and silicone resin, but it is preferred to use polyurethane that is excellent in biocompatibility.

In the present invention, the deoxidizer or oxygen absorber is held in a sealed container together with the medical module, and thus the deoxidizer is required to be nontoxic. In order to minimize extractables from the hollow fibers due to damages by irradiation, preferably, the deoxidizer is a deoxidizer or an oxygen absorber of a water-releasing type that releases water at the time of absorption of oxygen. Further, it is preferred that the deoxidizer contains an active metal as a main component and has a controllable reaction rate with a catalyst. Typical active metals include, for example, iron, zinc, copper and tin. It is, however, preferred to use a deoxidizer comprising activated iron oxide in view of cost and deodorizing effects. Commercially available water-releasing type deoxidizers are exemplified by SANSOCUT (Trademark, Nittetsu Fine Products, Co. Ltd.), AGELESS (Trademark for oxygen absorber, Mitsubishi Gas Chemical Company, Inc.) and TAMOTSU (Trademark for oxygen absorber, OJITAC CO., LTD.).

As a gas-impermeable material for the sealed container holding the hollow fiber blood-processing device and the deoxidizer, it is preferred to use a material with an oxygen-permeability of 1 $cm^3/(m^2 \cdot 24\ h \cdot atm)$ or below, and a vapor-permeability of 5 $g/(m^2 \cdot 24\ h \cdot atm)$ or below. Such a gas-impermeable material include, for example, oriented or unoriented films or sheets of polyvinylidene chloride, polyvinyl alcohol, polyamides and polyesters; films or sheets coated with these resins; laminated films or sheets of these films; laminated films or sheets of polyester/aluminum/polyethylene; four-layered, laminated films or sheets of polyethylene terephthalate/polyethylene/aluminum/polyethylene or nylon/polyethylene/aluminum/poly-ethylene; metal foils such as aluminum foil; deposited metal films such as deposited aluminum films, and laminated products of these films. The preferred materials are four-layered, laminated films of polyethylene terephthalate/polyethylene/aluminum/polyethylene or nylon/polyethylene/aluminum/polyethylene.

In the present invention, the term "radiation sterilization" means a method for radiation sterilization of gamma rays or electron rays. The radiation sterilization has various advantages: The sterilization can be applied to end products in which the product to be sterilized is held in a sealed container. Since the radiation sterilization can be carried out at the normal temperature, there is no fear of damages or degradation of the materials that may occur by the sterilization at elevated temperatures. Since there is no fear of formation of noxious residues such as noxious gases, the radiation sterilization is a safe method of sterilization. Further, it is easy to control the sterilization process, thus making it possible to continuously sterilize large quantities of products under the same conditions.

The irradiation of gamma rays may be carried out under the normally used conditions. It is sufficient for the sterilization to perform irradiation with 5 to 40 kGy, preferably, 10 to 20 kGy of gamma rays.

The hollow fiber blood-processing device generally divided into two types, i.e., an apparatus of the kind wherein a container that houses a hollow fiber bundle is filled with a liquid such as sterile water or distilled water (herein after referred to as a "wet type"), and an apparatus of the kind wherein a container that houses a hollow fiber bundle is not filled with a liquid (herein after referred to as a "dry type"). It is preferred to use a dry type. Because, the wet type has an increased weight and disadvantages for handling or transportation. In addition, there is a fear of freezing in winter seasons. Further, it is necessary for the wet type to prepare the liquid such as sterile water to be charged in the container, thus making it difficult to save the production cost of the blood-processing device. In addition, since the hollow fibers are held in the wet conditions that are easy for bacteria to bleed, there is a fear of bleeding of bacteria even in a short time before sterilization but after sealing. Thus, the production of the wet type requires any refrigerating plant to prevent the hollow fibers from being bleeding of bacteria. In contrast therewith, the dry type blood-processing device is free from the aforesaid problems since it contains no liquid in the container.

In the dry type blood-processing device, an interior of a cylindrical container (i.e., a space holding the hollow fibers) is filled with a gas without any restriction of its constituents. Thus, the gas may be an atmospheric air that contains oxygen even at the time of sealing the gas impermeable container holding the blood-processing device. However, when performing radiation sterilization, it is preferred to keep the interiors of the sealed container and blood-processing device free from oxygen. This may be done by holding the hollow fibers together with a deoxidizer in the sealed container of the gas-impermeable material. The deoxidizer which absorbs oxygen in the sealed container is a water-releasing type deoxidizer.

According to the present invention, it is possible to produce hollow fiber blood-processing devices with minimal extractables from the hollow fibers since the irradiation is carried out after holding the blood-processing device and the deoxidizer in the sealed container of the gas-impermeable material. Since the blood-processing device is kept in the oxygen free conditions before carrying out the radiation sterilization, it is possible to produce hollow fiber blood-processing devices with minimal extractables from the hollow fibers even if the hollow fibers are made of polysulfone-based resin containing hydrophilic polymer. In addition, the extractables from the hollow fibers are considerably reduced by use of the water-releasing type deoxidizer.

Further, since the oxygen released from the hollow fibers are absorbed by the water-releasing deoxidizer, the present invention makes it possible to improve the shelf life of the blood-processing device even if the hollow fibers are of polysulfone-based resin that releases adsorbed oxygen during storage.

The present invention will become more fully understood from the detailed description given below as an embodiment thereof.

BRIEF DESCRIPTION OF THE DRAWINGS

FIG. 1 is a cross section of a hollow fiber blood-processing device embodying the present invention.

PREFERRED EMBODIMENT OF THE INVENTION

Referring now to FIG. 1, there is shown a blood-processing device (1) of a hollow fiber membrane type, which comprises a bundle (2) of a plurality of hollow fiber membranes, a cylindrical container (3) holding the hollow fiber bundle (2) therein. The cylindrical body (3) has an inlet port (4) and an outlet port (5) each arranged in the proximity of each end of the cylindrical body (3). Caps (6, 7) are mounted on each end of the cylindrical body (3) and provided with an inlet (8) and an outlet (9). The hollow fiber membranes are made of, for example, polyethersulfone containing polyvinylpyrollidone, bundled together to form a hollow fiber bundle (2), inserted into the cylindrical body (3) and sealed at both ends thereof by a potting material 10. The cylindrical body (3) is formed with a uniform inner diameter D1 between the inlet (8) and the outlet (9), and the hollow fibers are held in positions parallel to each other such that the bundle (2) of hollow fibers has an outer diameter along an entire length thereof that is substantially equivalent to the inner diameter D1 of the cylindrical body (3). The inlet (8) and the outlet (9) are provided on portions of the cylindrical body (3) where the inner diameter of the cylindrical container is D2, where D2 and D1 have the relationship D2>D1.

The blood-processing device (1) is packaged in a gas-impermeable container (11) together with a deoxidizer (12) and then radiation sterilized in the following manner.

The hollow fiber blood-processing device (1) is put into the gas-impermeable container (11) together with the oxygen absorber (12) of a water-releasing type. The gas-impermeable container is made of, for example, a four-layered laminated film of nylon/polyethylene/aluminum/poly-ethylene. The container (11) is then sealed by thermal welding, and left to stand for a number of hours, preferably 12 hours or more, more preferably, 24 hours or more so that the interior of the container is made into an oxygen-free state. Then, the sealed container (11) is subjected to radiation sterilization to complete the sterilization.

An embodiment of the present invention will be given below. However, the present invention is not limited thereto.

EXAMPLE 1

Using hollow fibers made of polyethersulfone containing PVP with an internal diameter of 200 μm and a film thickness of 30 μm, there are prepared hollow fiber blood-processing devices by bundling 9600 pieces of hollow fibers to form a hollow fiber bundle, inserting the hollow fiber bundle into a cylindrical container of polycarbonate, injecting a polyurethane potting material into both ends of the cylindrical container to seal the both ends thereof, cutting away some parts of the hollow fiber bundle from both ends thereof together with extra potting materials to allow the hollow fibers to be opened at both ends thereof, and mounting headers on both ends of the container to complete the hollow fiber blood-processing device of a dry type. The blood-processing device is placed into a container made of a gas-impermeable material, i.e., a laminated film of polyester/aluminum/polyethylene together with an oxygen absorber, SANSOCUT (Trademark, Nittetsu Fine Products, Co. Ltd.). After sealing the container in the atmosphere, the container is left to stand for about 24 hours to allow the oxygen absorber to absorb oxygen in the sealed container to make the interior of the container into an oxygen-free state. The sealed container is then radiation sterilized by exposure to gamma rays of 15 kGy.

In accordance with the aforesaid standards for approval of artificial kidneys, a test solution for extraction of the hollow fibers in the sterilized hollow fiber blood-processing device is prepared, and then subjected to measurement of absorbance. Result is shown in Table 1.

COMPARATIVE EXAMPLE 1

There were prepared hollow fiber blood-processing devices of a dry type in the same manner as in Example 1. Each device was put into a gas-impermeable container made of a laminated film of polyester/aluminum/polyethylene without use of any oxygen absorber. After sealing the container in the atmosphere, the sealed container is then radiation sterilized by exposure to gamma rays of 15 kGy.

There was prepared a test solution for extraction of the hollow fibers taken from the sterilized hollow fiber blood-processing device in accordance with the aforesaid approval standards for artificial kidneys. The test solution for extraction was then subjected to measurement of absorbance. The result is shown in Table 1.

TABLE 1

| | OXYGEN ABSORBER | ABSORBANCE |
|---|---|---|
| Example 1 | Present | 0.055 |
| Comparative Example 1 | None | 0.285 |

(Common Conditions)
Type of hollow fiber blood-processing device: Dry type
Material of hollow fibers: Polyetersulfone containing PVP

| | |
|---|---|
| Film thickness of hollow fibers: | 30 μm |
| Internal diameter of hollow fibers: | 200 μm |

-continued

| | |
|---|---|
| Gamma radiation: | 15 kGy |
| Material for gas-impermeable container: | polyester/aluminum/polyethylene |
| Time to radiation sterilization after sealing: | 24 hours |

As shown in Table 1, when the blood-processing device comprising hollow fibers of Polyetersulfone containing PVP is packaged alone in the sealed gas-impermeable container and radiation sterilized, the absorbance of the test solution for extraction is 0.285, which does not meet the approval standards for artificial kidneys mentioned above. In contrast therewith, in case of the blood-processing device of Example 1, which was packaged together with the water-releasing type deoxidizer in the sealed gas-impermeable container and radiation sterilized, the absorbance of the test solution for extraction is 0.055. Thus, by sealing the blood-processing device together with the water release deoxidizer in the gas-impermeable container, it is possible to reduce the extractables from the hollow fibers after radiation sterilization, thus making it possible to produce hollow fiber blood-processing devices that meet approval standards for artificial kidneys defined in "The Japanese Pharmacopoeia Fourteenth Edition".

What is claimed is:

1. A packaged blood purification device comprising:
a hollow fiber blood-processing device including a bundle of hollow fibers and a cylindrical container holding said bundle of hollow fibers;
a water-releasing oxygen absorber; and
a gas impermeable container,
wherein said hollow fiber blood-processing device and the water-releasing oxygen absorber are packaged and sealed within the gas impermeable container, and
within the gas impermeable container, only a substantially oxygen-free gas separates the cylindrical container of the hollow fiber blood-processing device from the water-releasing oxygen absorber, such that the cylindrical container of the hollow fiber blood-processing device and the water-releasing oxygen absorber are directly exposed to each other through the substantially oxygen-free gas,
wherein each of said gas impermeable container, said hollow fiber blood-processing device, and said water-releasing oxygen absorber has been subjected to sterilization,
wherein the cylindrical container includes a single inlet port projecting and opening sideways adjacent to one end of the cylindrical container, and a single outlet port projecting and opening sideways from at an opposite end of the cylindrical container,
wherein the cylindrical container has an outer circumferential wall which directly faces inner walls of gas impermeable container,
wherein said hollow fibers include an amount hydrophilic polymer in a range of 3% to 20% by weight.

2. The packaged blood purification device according to claim 1, wherein interiors of the blood-processing device and an interior of said gas impermeable container are in an oxygen-free state.

3. The packaged blood purification device according to claim 1, wherein the blood-processing device is a dry blood-processing device.

4. The packaged blood purification device according to claim 1, wherein the blood-processing device is radiation sterilized by gamma radiation.

5. The packaged blood purification device according to claim 1, wherein said hollow fibers are made of a polysulfone-based resin including the hydrophilic polymer, and
wherein said hydrophilic polymer is a polyvinyl pyrrolidone.

6. The packaged blood purification device according to claim 1, wherein said polysulfone-based resin is polysulfone.

7. The packaged blood purification device according to claim 1, wherein said polysulfone-based resin is polyethersulfone.

8. The packaged blood purification device according to claim 1, wherein the bundle of hollow fibers includes 7000 to 12000 hollow fibers.

9. The packaged blood purification device according to claim 1, wherein portions of the hollow fibers are viewable when viewed along axes of the single inlet and the single outlet from positions outside the cylindrical container.

10. The packaged blood purification device according to claim 1, wherein the cylindrical container is formed with a uniform inner diameter D1 between the inlet port and the outlet port,
wherein hollow fibers are held in positions parallel to each other such that the bundle of hollow fibers has an outer diameter along an entire length thereof that substantially equivalent to the inner diameter D1 of the cylindrical container,
wherein the single inlet port and the single outlet port project from portions of the cylindrical container where the inner diameter of the cylindrical container is D2,
wherein D2 and D1 have the relationship D2>D1.

11. The packaged blood purification device according to claim 1, wherein each of the two ends of the cylindrical container is provided with an end cap, one of which abuts the single inlet port, and the other of which abuts the single outlet port.

12. The packaged blood purification device according to claim 1, wherein the gas impermeable container is made of a four-layer laminated film of nylon/polyethylene/aluminum/poly-ethylene.

13. The packaged blood purification device according to claim 1, wherein said hollow fibers have inner diameters of 100 to 120 μm.

* * * * *